United States Patent
Nakasuji

(10) Patent No.: US 6,465,783 B1
(45) Date of Patent: Oct. 15, 2002

(54) HIGH-THROUGHPUT SPECIMEN-INSPECTION APPARATUS AND METHODS UTILIZING MULTIPLE PARALLEL CHARGED PARTICLE BEAMS AND AN ARRAY OF MULTIPLE SECONDARY-ELECTRON-DETECTORS

(75) Inventor: Mamoru Nakasuji, Yokohama (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 09/587,165

(22) Filed: Jun. 2, 2000

(30) Foreign Application Priority Data

| Jun. 24, 1999 | (JP) | ............................. 11-178014 |
| Nov. 5, 1999 | (JP) | ............................. 11-314876 |
| Apr. 24, 2000 | (JP) | ............................. 2000-122291 |

(51) Int. Cl.⁷ ............................. G01N 23/00; G21K 7/00
(52) U.S. Cl. ..................... 250/311; 250/306; 250/307; 250/310
(58) Field of Search ................... 250/306, 310, 250/492.2, 492.1, 492.22, 307, 311

(56) References Cited

U.S. PATENT DOCUMENTS 4,893,009 A * 1/1990 Kuroda .................. 250/310
5,939,725 A * 8/1999 Muraki .................. 250/492.22
5,981,962 A * 11/1999 Groves et al. ......... 250/492.23

* cited by examiner

Primary Examiner—John R. Lee
Assistant Examiner—David A. Vanore
(74) Attorney, Agent, or Firm—Klarquist Sparkman, LLP

(57) ABSTRACT

Apparatus and methods are disclosed for inspecting semiconductor wafers and other types of specimens using parallel charged particle beams (e.g., electron beams). An emitter array, including multiple charged-particle-beam (CPB) emitters produces multiple beams that propagate along respective beam axes. The beams pass simultaneously through projection lenses and a deflector so as to cause the beams to be focused simultaneously onto respective loci on the surface of the specimen so as to cause each locus to emit secondary electrons. The secondary electrons are detected by a secondary-electron (SE) array including multiple SE-detector units. Each SE detector unit receives and detects secondary electrons emitted from a respective locus. The deflector simultaneously scans the beams over respective regions on the specimen surface. Each SE detector is configured to detect secondary electrons but not backscattered electrons emitted from the respective locus. Alternatively, multiple channels can be provided, each channel corresponding to a respective beam. Each channel includes a respective set of lenses and deflectors for the respective beam. The channel pitch is adjustable to accommodate various die pitches on the specimen.

35 Claims, 9 Drawing Sheets

HIGH-THROUGHPUT SPECIMEN-INSPECTION APPARATUS AND METHODS UTILIZING MULTIPLE PARALLEL CHARGED PARTICLE BEAMS AND AN ARRAY OF MULTIPLE SECONDARY-ELECTRON-DETECTORS

FIELD OF THE INVENTION

This invention pertains to apparatus and methods for manufacturing semiconductor devices, displays, and the like. More specifically, the invention pertains to apparatus and methods for inspecting wafers and analogous substrates at any of various times during a wafer-fabrication procedure. Even more specifically, the invention pertains to such methods and apparatus that utilize an electron beam that is scanned over at least a portion of the wafer surface in order to reveal surficial detail of the wafer, including surface features having dimensions of 0.2 $\mu$m or less.

BACKGROUND OF THE INVENTION

During the manufacture of integrated circuits, displays, and the like on a semiconductor wafer or other suitable substrate, it is necessary at various steps to inspect the wafer for defects. Inspections are also required when manufacture is complete, before the wafer is cut ("diced") into individual chips or other units. Inspections are indispensable for improving yield and avoiding the shipping of defective goods.

Much wafer inspection is still performed using optical microscopes employing light to illuminate the wafer, wherein defects are detected from characteristics of light reflected from the wafer. I.e., the wafer surface is imaged using an optical microscope. The magnified image is compared with a reference pattern by means of video processing. In view of the resolution limits of light-based microscopy, these methods have increasingly limited applicability, especially with wafers on which the critical dimension is 0.2 $\mu$m or less.

To obtain better resolution than obtainable with optical microscopy, electron-beam scanning apparatus have been used for inspecting wafers in the manner of a scanning electron microscope. In a conventional electron-beam apparatus, a single electron beam (focused to a point) is scanned in a raster manner over a selected portion of the wafer. When irradiated in such a manner, the wafer emits secondary electrons and backscattered electrons from the point of irradiation. The secondary and/or backscattered electrons are detected, and the presence of surficial defects can be determined from the resulting pattern of detected electrons.

Although conventional scanning-electron-beam inspection apparatus are capable of resolving detail measuring 0.2 $\mu$m or less, the fact that scanning is performed using a single, narrowly focused beam results in very low inspection throughput due to the long scanning time required per wafer. Consequently, these apparatus are impractical for high-throughput wafer fabrication. Rather, they are relegated to use for supplementary defect inspection in testing situations.

This problem is circumvented somewhat simply by performing sampling inspections (in which not all wafers or only portions of wafers actually are inspected) using a scanning electron-beam apparatus. Unfortunately, this compromise results in an unacceptable amount of finished product being shipped that have major defects.

SUMMARY OF THE INVENTION

In view of the shortcomings of the prior art as summarized above, an object of this invention is to provide inspection methods and apparatus that achieve high-throughput inspection of specimens, such as semiconductor wafers and other substrates, using a charged particle beam such as an electron beam. Another object is to provide manufacturing methods, for semiconductor devices, that include such inspection methods.

To such ends, and according to a first aspect of the invention, apparatus are provided for inspecting a surface of a specimen. An embodiment of such an apparatus comprises an emitter array, first and second electromagnetic lenses, a secondary electron (SE)-detector array, and a deflector. The emitter array comprises multiple charged-particle emitters (e.g., electron-beam emitters) each configured to emit simultaneously a separate individual charged particle beam along a separate respective beam axis. The first and second electromagnetic lenses are situated downstream of the emitter array. The lenses are configured to focus simultaneously the individual charged particle beams, from the emitter array, onto respective loci on the surface of the specimen so as to cause each of the loci to emit secondary electrons. The secondary-electron (SE)-detector array comprises multiple SE-detector units each situated and configured to receive and detect secondary electrons from a respective locus on the specimen. The deflector is situated between the first and second electromagnetic lenses and is configured to deflect the charged particle beams and cause the beams to scan simultaneously respective regions on the surface corresponding to the respective loci.

In this embodiment, deflection and scanning of the individual charged particle beams can be performed by a single deflector, which imparts the same deflection and scanning to all the beams. Individual respective SE detectors detect the secondary electrons from the various loci. The SE detectors desirably are configured such that "crosstalk" between the various SE detectors is negligible.

The scanning range of each charged particle beam is determined by the deflector and other components of a charged-particle-beam (CPB) optical system used to direct and focus the individual beams on their respective loci. Respective regions about the loci are inspected by scanning the respective beams within a defined range. Areas outside the regions are inspected simply by moving the specimen to within the scanning range of the charged particle beams.

The emitter array can be in one dimension (linear array). However, such an array requires that the specimen be moved continuously to obtain a two-dimensional scanning range. A two-dimensional emitter array allows less movement of the substrate, and permits (for example) inspection using a step-and-repeat scheme.

The first and second electromagnetic lenses can be configured as a symmetric magnetic doublet (SMD), which is a type of electromagnetic lens assembly used to form an image of the emitter array on the surface of the specimen. An SMD is advantageous because it minimizes the occurrence of aberrations and improves the perpendicular incidence properties of the individual charged particle beams on the specimen surface. The SMD can be a magnifying lens or 1:1 (non-magnifying and non-reducing) lens. A 1:1 lens provides excellent control of aberrations but can pose difficulties in arranging the individual SE detector units. A magnifying lens allows the emitter array to be made smaller.

The SMD further can comprise a magnification-adjusting lens.

Such a lens allows the pitch of the CPB emitters, as projected onto the specimen to be adjusted to some extent to match the pitch of, e.g., dies on the specimen. It is also possible to have various SE-detector arrays available that match the die pitch of any of several types of specimens to be inspected, wherein the array having the correct pitch can be selected for use with a particular specimen.

The charged-particle emitters of the emitter array can be in an X-Y plane (wherein the beam axes extend in a Z-direction). Alternatively, the charged-particle emitters can be displaced individually from the X-Y plane so as to correct curvature of an image collectively formed on the specimen by the charged particle beams passing through the first and second electromagnetic lenses. The most pronounced aberration in CPB optical systems using an SMD is image curvature. By shifting the respective positions of the various charged-particle emitters in the Z-direction, effects of image curvature can be reduced greatly or eliminated.

The loci typically are arrayed on the surface of the specimen with an X-direction pitch and a Y-direction pitch. Desirably, at least one (more desirably both) of the X-direction pitch and the Y-direction pitch is adjustable. Such an adjustment allows the pitch used for inspection to be adjusted to match the pitch of, e.g., dies on the surface of the specimen.

Further desirably, each SE-detector unit in the SE-detector array comprises a respective detector electrode in surrounding relationship to the respective beam axis. Each detector electrode is energized with a respective voltage. Each detector electrode also defines a respective through-hole. An SE detector is situated outside the respective detector electrode adjacent the through-hole, and charged with a voltage that is more positive than the respective voltage with which the respective detector electrode is energized. This potential profile draws secondary electrons through the through-hole to the respective SE detector. By effectively surrounding each locus with respective electrodes, secondary electrons emitted from the locus do not propagate outside the electrodes. By situating the SE detector, having a relatively high positive potential, outside the respective electrode and adjacent the through-hole, secondary electrons are drawn to the SE detector by an electrical field that extends through the hole into the space surrounded by the respective electrode. This configuration is highly favorable to capture and detection of the secondary electrons emitted from the respective locus, with minimal crosstalk between the various SE detectors. This configuration also effectively captures secondary electrons propagating in virtually any direction from the respective locus to be gathered to the respective SE detector, thereby making highly accurate defect inspection possible.

Each through-hole has a particular angular orientation about the respective beam axis. Desirably, the angular orientations of the through-holes are identical for all SE detectors of the SE-detector array. As summarized above, the electrical field produced by the potential impressed on an SE detector extends through the hole into the interior of the electrode. The respective charged particle beam is deflected by this field. If the angular orientations of the through-holes in the various electrodes were random relative to each other, then beam-deflection magnitudes and directions within the various electrodes would be different one to another. This would cause the various scanning beams to have a different profile when scanned, requiring the respective locus to be determined individually for each respective SE detector. This, in turn, would require more complex data processing and correction deflectors as required for individual beams. By disposing all the through-holes with the same angular orientation relative to the respective beam axis, the shape of the electrical field inside each electrode is the same, allowing all the beams to be deflected in the same manner. This allows for linear scanning, and the use of a single deflector to provide any needed compensation of deflection magnitude.

Each SE-detector unit desirably comprises a respective SE detector and scintillator associated with the SE detector. In such a configuration, each scintillator is connected by a light guide to a photodetector. Most of the components of the inspection apparatus (e.g., the emitter array, SMD, deflector, SE-detector array) are contained in a vacuum chamber. In an SE-detector including a scintillator and a photodetector, it is desirable that the photodetector (e.g., a photomultiplier tube) be located outside the vacuum chamber. Light is conducted from the scintillator via a light guide through a transparent window in the vacuum chamber to the photodetector. This allows the total size of components disposed inside the vacuum chamber to be minimized.

The apparatus summarized above also can include a respective scanning-position deflector for each beam. Such a deflector is configured to scan the respective charged particle beam within a respective area, corresponding to the respective locus, on the surface of the specimen. The respective scanning-position deflector can be situated upstream or downstream of the respective SE detector. Even though all the beams are deflected in the same manner by the deflector discussed above, the presence of an additional deflector for each beam allows small corrections to be applied to each beam as required, especially when performing inspections over a wide area of the specimen without moving the specimen.

According to another aspect of the invention, methods are provided for inspecting a surface of a specimen. In an embodiment of such a method, multiple separate individual charged particle beams are produced, each propagating along a respective beam axis. The individual charged particle beams are focused simultaneously onto respective loci on the specimen surface so as to cause each of the loci to emit secondary electrons. While focusing the beams, the charged particle beams are deflected simultaneously so as to cause each beam to scan a respective region corresponding to the respective locus. The secondary electrons produced from each region are detected so as to produce respective signals pertaining to the secondary electrons emitted from the regions. The signals are analyzed to produce data from which an image of the scanned regions of the surface can be formed.

The method summarized above can be used in a process for manufacturing semiconductor devices on a wafer substrate. Specifically, the method can be used for inspecting the wafer substrate at various times during wafer processing, for example. Such inspections can be performed even if the wafer substrate has die patterns having minimum linewidths of less than 0.2 $\mu$m, and can be performed with good throughput. Furthermore, every die on every wafer can be inspected.

According to another aspect of the invention, apparatus are provided for inspecting a surface of a substrate on which multiple dies have been formed at an X-direction die pitch and a Y-direction die pitch. An embodiment of such an apparatus comprises an emitter array, a projection-lens system, and an SE-detector array. The emitter array comprises multiple charged-particle emitters each configured to emit a separate individual charged particle beam along a respective beam axis extending in a Z-direction. The beams collectively have an X-direction beam pitch and a Y-direction beam pitch. The projection-lens system is situated and configured to focus simultaneously the individual charged particle beams, from the emitter array, onto respective loci on the surface of the substrate so as to cause the loci to emit secondary electrons. The SE-detector array comprises multiple SE-detector units each situated and configured to receive and detect secondary electrons from a respective locus on the substrate. At least one of the X-direction die pitch and Y-direction die pitch is an integer multiple or integer fraction of the X-direction beam pitch and Y-direction beam pitch, respectively.

Whenever the beam pitch is an integer multiple of the die pitch, all of the beams are irradiated under the same conditions onto the specimen. Also, the data obtained from all of the SE detectors can be processed in the same way, allowing multiple dies to be inspected at one time. This allows inspection time to be reduced substantially with simple control.

Whenever the die pitch is a multiple of the beam pitch, one die can be inspected using multiple beams. This allows inspection to be performed at even higher throughput, further shortening inspection time.

Another apparatus embodiment includes an emitter array as summarized above. The apparatus includes multiple SE columns situated and configured to direct a respective individual charged particle beam to a respective locus on the surface of the substrate so as to cause the loci to emit secondary electrons. Each SE column comprises a respective SE-detector unit situated and configured to receive and detect secondary electrons from the respective locus. Thus, each SE column accommodates one respective beam. In the SE column, the respective beam is produced, deflected, and irradiated by a respective source, deflectors, and lenses. Multiple beams are formed by using multiple SE columns. Hence, column design is easy and simple. Also, inspection time is shortened because multiple beams are used for inspection.

Yet another embodiment of an apparatus comprises a field-emitter array comprising multiple electron emitters each configured to emit a separate individual electron beam along a respective beam axis. The apparatus also includes a projection-lens system and an SE-detector array. The projection-lens system is situated and configured to focus simultaneously the individual electron beams, from the field-emitter array, onto respective loci on the surface of the substrate so as to cause the loci to emit secondary electrons. The SE-detector array comprises multiple SE-detector units each situated and configured to receive and detect secondary electrons from a respective locus on the substrate.

In a field-emitter array, each emitter comprises a tip with a sharp point and a drawing electrode (gate) that surrounds the tip. See, e.g., "Field Emitter Tip Research: Present and Future," presented at the Charged Particle Beam Optics Symposium, $132^{nd}$ Meeting of the Committee on the Industrial Application of Charged Particle Beams, Japanese Science Society (Oct. 29–30, 1988). By impressing a positive potential of several volts on the gate, a strong electrical field of $10^7$ V/cm is generated in the tip. Also, the vacuum barrier (work coefficient) is reduced to about 1 nm, causing tunneling electrons to be emitted into the vacuum.

Field-emitter arrays can be manufactured using fine-processing techniques employing microlithography. Thus multiple-CPB sources can be manufactured easily and precisely. Also, as discussed in the paper cited above, stable emission currents can be realized by producing individual tips as a transistor structure.

According to another aspect of the invention, an improved SE detector is provided for use in an apparatus for inspecting a surface of a substrate (in which apparatus a charged particle beam is irradiated along a beam axis onto a beam-irradiation locus in a beam-irradiation region on the surface of the substrate to cause the beam-irradiation region to emit secondary electrons). The SE detector comprises first and second electrode members situated peripherally relative to the beam-irradiation region such that the first and second electrode members face the beam axis and each other across the beam-irradiation region. The first electrode member is charged with either a ground potential or a negative potential. The second electrode member is charged with a positive potential so as to direct the secondary electrons toward the second electrode member. Such a charging scheme directs the flow of secondary electrons toward the SE detectors.

By configuring a zero- or negative-potential member and a positive-potential member to face one another in the manner summarized above, secondary electrons are reflected from the member having the negative or zero potential and are collected on the member having a positive potential. The SE detector is placed adjacent the member on which the secondary electrons gather, thereby increasing detection sensitivity and inspection speed.

More specifically, the SE detector is situated radially outside the second electrode member. In such a configuration, the second electrode member defines a through-hole, and the SE detector is situated adjacent the through-hole and charged with a positive potential higher than the positive potential with which the second electrode member is charged. This urges secondary electrons to pass through the through-hole to the detector.

Further desirably, the SE detector is situated relative to the through-hole such that backscattered electrons emitted along respective linear trajectories from the beam-irradiation region do not impinge on the SE detector. The first and second electrode members are configured to block propagation therethrough of backscattered electrons. By blocking backscattered electrons in this manner, the backscattered electrons are not detected by the SE detector and thus do not become noise. Meanwhile, secondary electrons passing through the hole are drawn to the positive potential impressed on the SE detector and are captured by the SE detector. Even though a few backscattered electrons pass through the hole, they have high kinetic energy. Hence, the trajectory of the backscattered electrons passing through the hole is unaffected by the positive potential of the SE detector and their trajectories are unchanged. Any possible effects of backscattered electrons are avoided by placing the SE detector where it will not be struck by backscattered electrons passing through the hole. This allows for a high signal-to-noise (S/N) ratio and high-speed inspection.

In yet another embodiment of an apparatus according to the invention, multiple CPB channels are situated and configured to emit simultaneously multiple charged particle beams each along a respective beam axis to a respective locus on the substrate surface so as to cause the loci to emit secondary electrons. The channels are arranged at a channel pitch in the X-direction and the Y-direction. Each channel comprises a CPB source (e.g., electron emitter), CPB lenses, a deflector, and an SE detector. The CPB lenses focus the respective beam as a respective beam spot on the respective locus. The deflector scans the beam spot within a respective region associated with the locus on the substrate surface. The SE detector detects the secondary electrons emitted from the respective region. The apparatus also includes a pitch-adjustment mechanism associated with the channels. The pitch-adjustment mechanism is configured to change the channel pitch in at least one of the X- and Y-directions.

The substrate can be a semiconductor wafer on which multiple dies are formed at a certain pitch (die pitch). The channel pitch can be adjusted to 1/n (wherein n is an integer) of the die pitch. By making such an adjustment, the channel pitch and the die pitch can be made the same. Alternatively, for example, the die pitch can be made an integer multiple of the channel pitch, wherein each channel can inspect the same position in separate dies. Such a configuration facilitates the detection of normal and defective dies by comparing the data generated by each channel.

Desirably, each channel has an outside dimension of no greater than 30 mm in the X-direction or Y-direction. Such miniaturization is made possible in part by making at least one of the CPB lenses and deflectors electrostatic. Such miniaturization allows each die on the substrate to be inspected using a single respective channel.

Further desirably, each SE detector comprises an electrode and a scintillator. The electrode defines a through-hole and is energized with a positive charge. The scintillator is situated adjacent the through-hole but downstream with respect to the secondary electrons emitted from the respective region. The scintillator also is situated such that back-scattered electrons from the respective region and propagating along a linear trajectory through the through-hole do not impinge on the scintillator. A charged particle beam incident to the substrate experiences scattering both inside the substrate and above the substrate. Hence, backscattered electrons propagate at any of various angles from the substrate surface. Secondary electrons, in contrast, are emitted only from the locus of impingement. An electrode configuration as summarized above detects only the secondary electrons that pass through the small hole in the electrode, and does not detect any backscattered electrons. This greatly improves the S/N ratio.

The light produced by the scintillator desirably is collected and focused by a condenser element. The condenser element can be connected to an optical fiber that conducts the light to a remote photodetector.

According to another aspect of the invention, methods are provided for inspecting a surface of a specimen on which multiple dies have been formed at a die pitch extending in the X- and Y-directions. In an embodiment of such a method, multiple separate individual charged particle beams are produced each propagating along a respective beam axis perpendicular to the X- and Y-directions. The beam axes are arranged at a channel pitch. The individual beams are focused simultaneously onto respective loci on the specimen surface so as to cause the loci to emit secondary electrons. While focusing the beams, the beams are scanned simultaneously over respective regions corresponding to the respective locus. Secondary electrons produced from each region are collected and detected. The channel pitch is adjusted to be 1/n of the die pitch, wherein n is an integer.

Hence, the loci can be incident at the same position in each die. With respect to any two dies, the presence or absence of defects can be determined based on the presence or absence of a difference in the signals produced by secondary electrons emitted from the loci in the two dies. The channel pitch and the die pitch can be either the same, or the die pitch can be an integer multiple of the channel pitch. Each channel can be made incident to the same locus in dies at two different locations.

Alternatively, at least three beams can be made incident at a same position in separate respective dies on the specimen. In such a configuration, the signals produced by secondary electrons emitted from the separate respective dies are compared to determine any difference in the signals indicating a difference in the respective dies.

By comparing the signals from three or more locations, it can be determined in which die a defect is located. In other words, if the signals from two locations are the same and the signal from the third location is different, then it can be determined that the defect actually is in one location.

The foregoing and additional features and advantages of the invention will be more readily apparent from the following detailed description, which proceeds with reference to the accompanying drawings.

BRIEF DESCRIPTION OF THE DRAWINGS

FIGS. 2(a)–2(b) show a portion of the secondary-electron (SE)-detector array in the FIG.-1 embodiment, wherein FIG. 2(a) is a plan view of four SE-detector units in the SE-detector array, and FIG. 2(b) is an elevational section of two SE-detector units in the array.

FIGS. 3(a)–3(b) show an SE-detector unit according to the second representative embodiment, wherein FIG. 3(a) is an elevational section and FIG. 3(b) is a transverse section along the line A–A' in FIG. 3(a).

DETAILED DESCRIPTION

This invention is described below in the context of multiple representative embodiments. However, it will be understood that the invention is not limited to those embodiments.

First Representative Embodiment

Figure 1:
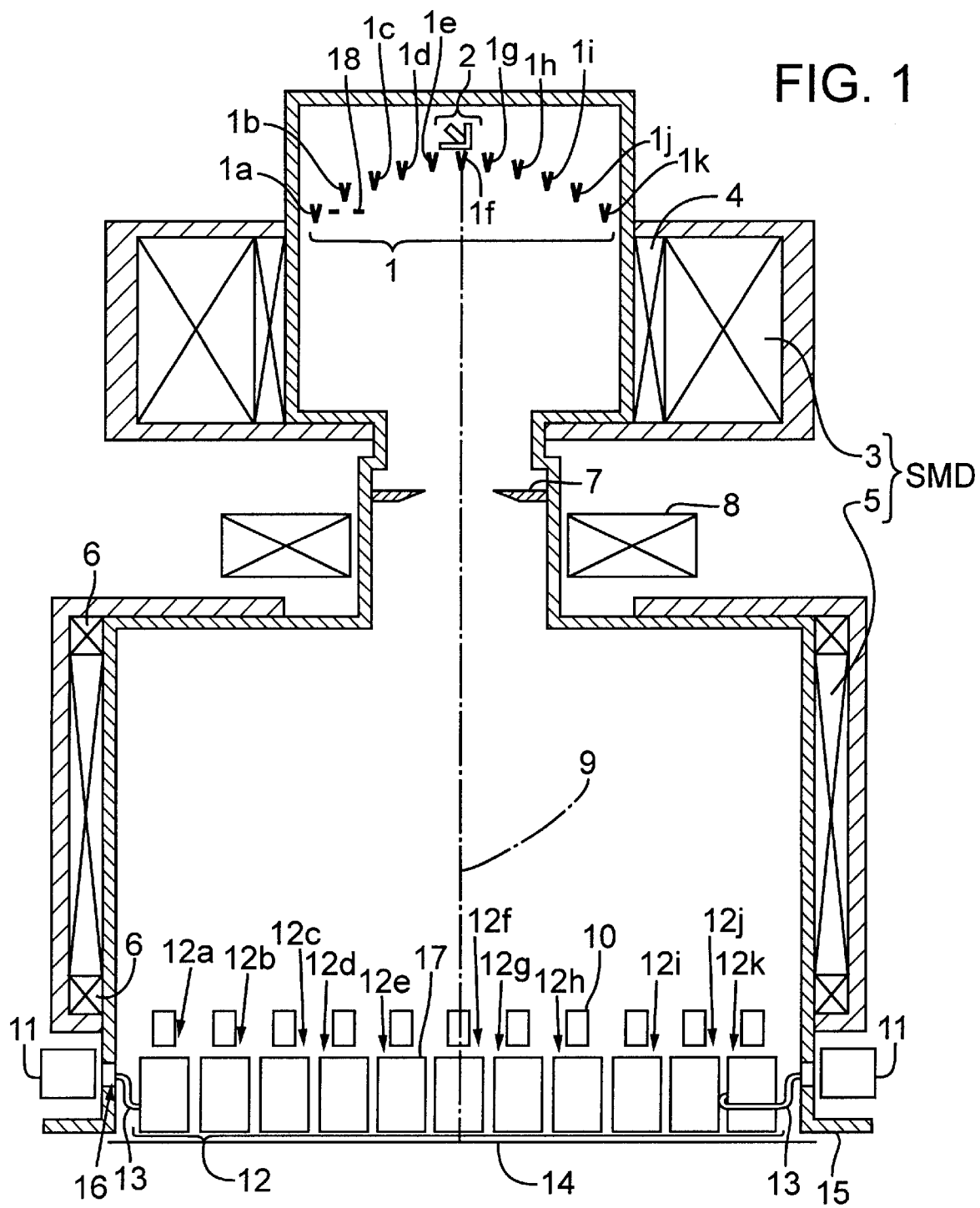
FIG. 1 is an elevational section of an electron-beam wafer-inspection apparatus according to a first representative embodiment of the invention.

An electron-beam inspection apparatus according to this embodiment is shown in FIG. 1. It is also noted that the FIG.-1 embodiment can be used to perform defect-inspection methods according to the invention.

The FIG.-1 embodiment comprises an electron-emitter array 1 comprising multiple individual electron-emission points 1a–1k, and a respective micro-drive mechanism 2 for each electron-emission point 1a–1k. The micro-drive mechanisms 2 are used for shifting the respective electron-emission point in the X, Y, and Z directions. Arranged along an axis 9 extending downstream of the emitter array 1 are a first projection lens 3, a first magnification-adjustment lens 4, a second projection lens 5, and a second magnification-adjustment lens 6. The first and second projection lenses 3, 5, respectively, desirably are configured as a "symmetric magnetic doublet" (SMD). Between the first projection lens 3 and the second projection lens 5 are a contrast aperture 7 and a scanning deflector 8. Downstream of the second magnification-adjustment lens 6 are an electrostatic deflector 10, a photomultiplier tube 11, a secondary-electron (SE)-detector array 12 comprising multiple individual SE-detector units 12a–12k, and light guides 13. The wafer is denoted by the reference numeral 14, and item 15 is a vacuum chamber that includes a window 16. Items 17 are respective cylindrical electrodes of individual SE-detector units 12a–12k of the SE-detector array 12. Each SE-detector unit 12a–12k corresponds to a respective emission point 1a–1k.

In the following description, the optical axis 9 is the Z-axis, which is one axis of the X, Y, Z Cartesian coordinate system used in the description.

In this embodiment, the electron-emission points 1a–1k of the electron-emitter array 1 are spaced nominally 10 mm apart in both the X- and Y-directions. Each electron-emission point 1a–1k emits a respective separate electron beam that passes through a respective beam-extraction anode 18. (Only one beam-extraction anode 18 is shown, associated with the electron-emission point 1b; however, in this embodiment, each electron-emission point 1a–1k has a respective beam-extraction anode 18 disposed immediately downstream of the respective emission point.) Each electron beam forms an image of its respective electron-emission point 1a–1k on the wafer 14 by the collective action of the first projection lens 3 and the second projection lens 5 functioning as an SMD. The SMD has a magnification ratio of 1:2 in this embodiment, by which is meant that the images formed by the SMD are twice as large as corresponding objects. Thus, the images of the respective electron-emission points 1a–1k, formed by the SMD on the wafer 14, are spaced 20 mm apart from each other in both the X- and Y-directions. Secondary electrons are emitted from the respective area of contact of each beam on the wafer 14.

Since the most pronounced aberration in an SMD is distortion, each electron-emission point 1a–1k of the emitter array 1 is disposed at a different position in the Z-direction, as shown in FIG. 1, which substantially corrects such aberrations. Fine adjustments of the individual electron-emission points 1a–1k can be performed as required using the respective micro-drive mechanisms 2 to further correct these and other aberrations. Such fine adjustments also can be made to correct residual positional errors, in the X- and Y-directions, of the individual electron-emission points 1a–1k that arise during manufacturing.

The electron beams emitted from the respective electron-emission points 1a–1k form a so-called crossover at a certain point on the axis 9. The contrast aperture 7 is disposed at the axial position of the crossover. The contrast aperture 7 must be sufficiently large so that the respective aperture angle of each electron beam (angle of the beam relative to the axis 9 as the beam passes through the crossover) is determined by the diameter of the opening defined by a respective beam-extraction anode 18. By making the respective aperture angles of the individual electron beams sufficiently small (below a threshold value), there is now need to correct image curvature, even if the respective focal points shift somewhat.

The scanning deflector 8, situated downstream of the contrast aperture 7, uniformly deflects all the individual electron beams so as to uniformly change the respective irradiation loci of the individual electron beams on the wafer 14. Thus, all the electron beams are uniformly and synchronously scanned over respective regions on the wafer 14. Since the respective aperture angles of the electron beams are determined by the respective beam-extraction anodes 18, the contrast aperture 7 can be relatively large and the scanning deflector 8 can be disposed at the position of the crossover, i.e., at the same axial position as the contrast aperture 7.

The scanning deflector 8 desirably is configured as a toroidal deflector having multiple coils. In such a configuration, each coil desirably is formed as printed wiring on a respective board substrate, and the board substrates are disposed radially around the axis 9.

Associated with the first and second projection lenses 3, 5 are the first magnification-adjusting lens 4 and the second magnification-adjusting lens 6, respectively. The magnification of the images formed by the electron beams can be adjusted by adjusting the respective electrical currents applied to the lenses 4, 6. For example, if the current applied to the first magnification-adjusting lens 4 is increased and the current applied to the second magnification-adjusting lens 6 is decreased, then image magnification is increased, thereby increasing the pitch of the individual electron beams at the surface of the wafer 14.

Each SE-detector unit 12a–12k comprises a respective cylindrical electrode 17. Each electrode 17 is situated so as to receive the respective electron beam. In this embodiment, each cylindrical electrode 17 is 16 mm in diameter, and the respective centers of the electrodes 17 are spaced 20 mm apart in the X- and Y-directions. The electrodes 17 are situated approximately 5 mm upstream of the wafer 14 in the Z-direction. Separate interchangeable SE-detector arrays 12 can be provided, each having a different pitch suited for a particular pitch of dies on a corresponding wafer 14 to be inspected. I.e., an appropriate SE-detector array 12 is selected for a particular dimensional arrangement of dies on a wafer to be inspected. In any event, the first and second magnification-adjusting lenses 4, 6, respectively, are adjusted as appropriate to obtain images of the electron-emission points 1a–1k of the electron-emitter array 1 at a pitch that matches the die pitch on the wafer 14.

Each SE-detector unit 12a–12k also includes a respective electrostatic deflector assembly 10. Each electrostatic deflector assembly 10 desirably is situated immediately upstream of the respective electrode 17. The deflector assemblies 10 are used individually to adjust the irradiation position of the respective electron beams on the wafer 14. The deflector assemblies 10 alternatively may be situated immediately downstream of the respective electrodes 17 (but still upstream of the wafer 14).

Figure 2A:
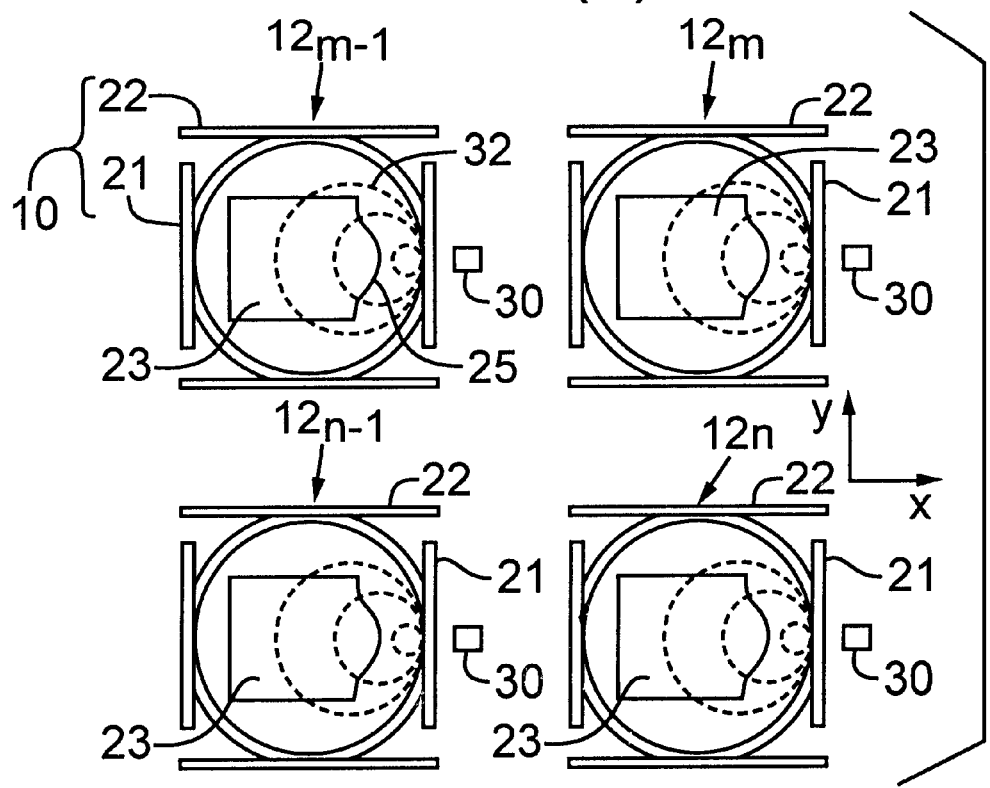
Figure 2B:
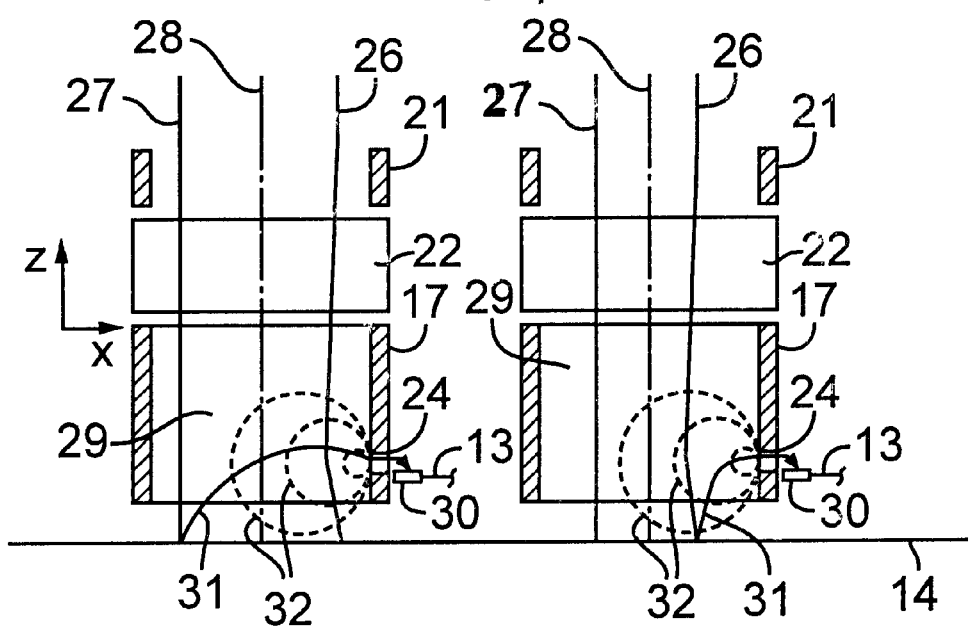

In this embodiment, it is desirable to minimize crosstalk in the respective outputs from the individual SE-detector units 12a–2k to a negligible level. FIGS. 2(a)–2(b) show a portion of the SE-detector array 12, wherein FIG. 2(a) is a plan view of four SE-detector units $12_{m-1}$, $12_m$, $12_{n-1}$, $12_n$ in the SE-detector array 12, and FIG. 2(b) is an elevational section of two SE-detector units in the array. In each individual SE-detector unit, the deflector assembly 10 comprises opposing pairs 21, 22 of electrostatic deflectors. Each region 23 is a respective scanning field for the corresponding SE-detector unit. Each scanning field 23 exhibits a scanning distortion 25. The lines 32 are respective equipotential lines discussed further below. In FIG. 2(b), each line 26 is a "corrected" trajectory of a respective electron beam, and each line 27 is the trajectory of a respective non-corrected electron beam through the interior space 29 of the respective electrode 17. Each line 28 is the optical axis of the respective SE-detector unit, and the lines 31 are representative trajectories of secondary electrons. Items 24 are respective small holes in the electrodes 17, and items 30 are respective scintillators.

In each SE-deflector unit, the electrostatic deflector assembly 10 comprises deflectors 21, 22 for performing deflection in the X-axis and Y-axis directions, respectively. The electrostatic deflector assemblies 10 allow individual adjustment of the position on the wafer 14 at which the respective beam is incident.

Each cylindrical electrode 17 defines a hole 24 having a diameter desirably of 1 to 2 mm. Each hole 24 is situated near the downstream edge of the respective cylindrical electrode 17. A respective scintillator 20 and light guide 13 are situated outside each electrode 17 near the respective hole 24. In this embodiment, a voltage of approximately −10 V is impressed on each electrode 17. Secondary electrons are repelled by the electrical field created by such a voltage, and thus exit the space 29 only through the hole 24. Hence, crosstalk between the electrodes 17 (each representing a respective"channel") is reduced greatly or eliminated.

Further with respect to this embodiment, a high positive voltage of approximately 20 KV is impressed on each scintillator 30. The electrical field generated by this voltage extends through the hole 24 into the interior space 29 of the respective electrode 17, creating a field represented by the equipotential lines 32. Secondary electrons propagate along respective trajectories such as those denoted by the numeral 31. Upon reaching the respective scintillator 30, the secondary electrons cause the scintillator 30 to generate corresponding light signals. The light signals are conducted by the light guide 13 to a photomultiplier tube 11 where the light signals are converted into corresponding electrical signals. With such a configuration, it is possible to gather secondary electrons separately that are emitted in all directions from the irradiation point of each beam.

The trajectory of each beam is susceptible to the deflecting action of the electrical field produced by the respective scintillator 30 and extending through the hole 24 into the interior space 29. The trajectory of a beam adjacent the side of the respective electrode 17 opposite the hole 24 is unaffected by this electrical field and propagates along the non-corrected path 27. The trajectory of a beam adjacent the side of the respective electrode 17 near the hole 24 extends toward the hole 24, causing the scanning distortion 25, even during linear scanning.

In this embodiment, the holes 24 in the cylindrical electrodes 17 are at the same positions and orientations in each SE-detector unit 12a–12k of the array 12. Hence, the scanning distortion 25 is the same for all the SE-detector units 12a–12k. This allows a common corrective action to be applied to all the SE-detector units 12a–12k using the scanning deflector 8. The scanning distortions 25 also can be corrected individually in each SE-detector unit 12a–12k using the respective electrostatic deflector assembly 10. In any event, these corrections produce a "corrected" beam trajectory in each SE-detector unit 12a–12k.

Further alternatively, common correction to all the beams can be performed by the scanning deflector 8, and fine adjustments to each beam can be performed using the respective electrostatic deflector assemblies 10.

If the holes 24 in the electrodes 17 of the SE-detector array 12 were not disposed identically and/or were not oriented identically, then scanning distortion 25 could not be corrected adequately using the scanning deflector 8. This would require that the scanning distortions be corrected individually using only the respective electrostatic deflector assemblies 10.

Field astigmatism also can be corrected using the electrostatic deflectors 21, 22 as an octapole. In addition, image curvature can be corrected by applying the same voltage to each electrode of the octapole.

The light from each scintillator 30 is conducted by the light guide 13 through a transparent window 16 in the vacuum chamber 15 into a nearby photomultiplier tube 11 situated outside the vacuum chamber 15.

The windows 16 (desirably one for each SE-detector unit 12a–12k in the SE-detector array 12) are disposed around the circumference of the vacuum chamber 15 (FIG. 1). Such a configuration allows the SE-detector units 12a–12k located inside the vacuum chamber to be as small as required. (Although only two light guides 13 are shown in FIG. 1, it will be understood that each SE-detector unit 12a–12k has a respective light guide.)

Second Representative Embodiment

Figure 3A:
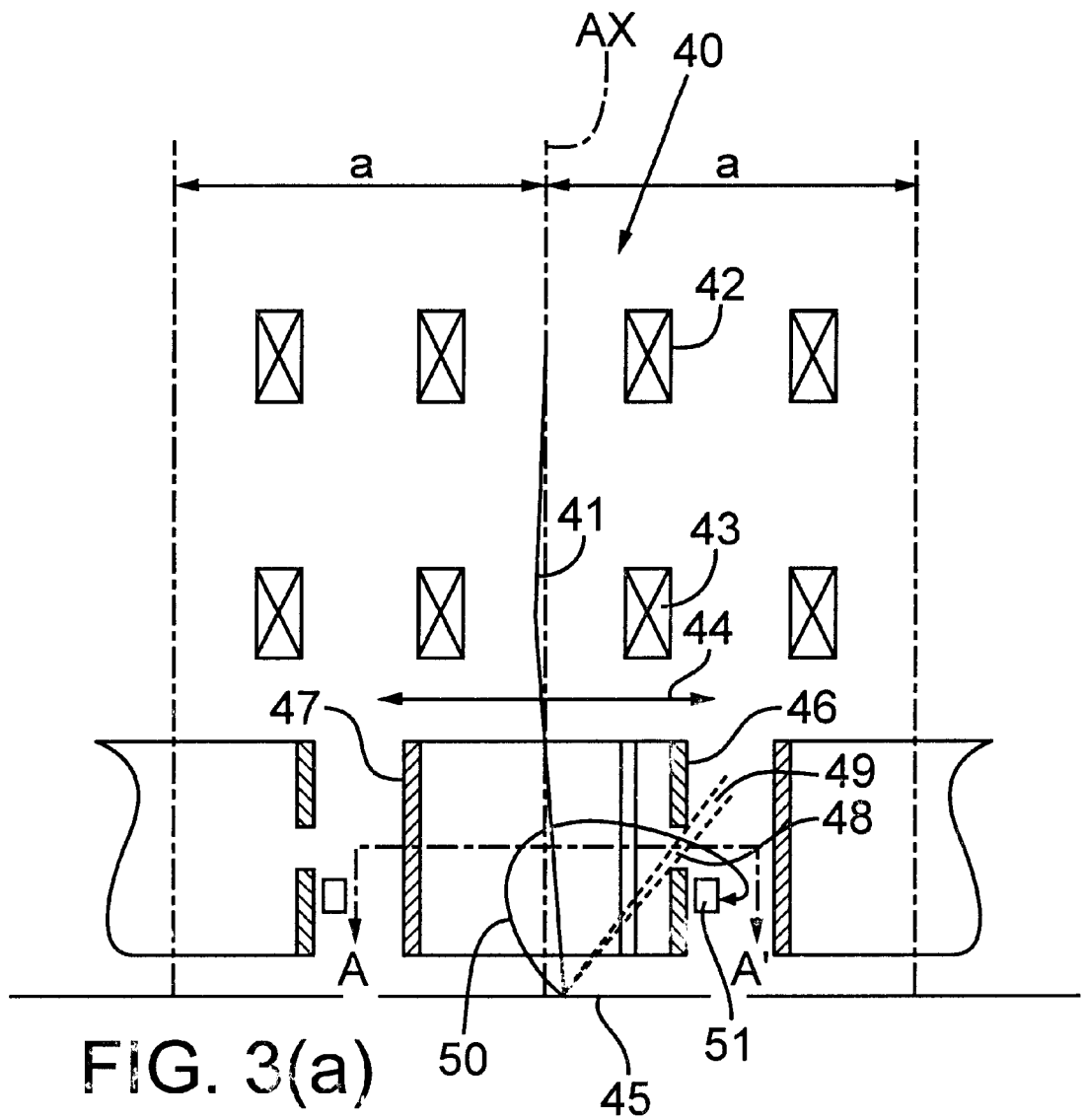
Figure 3B:
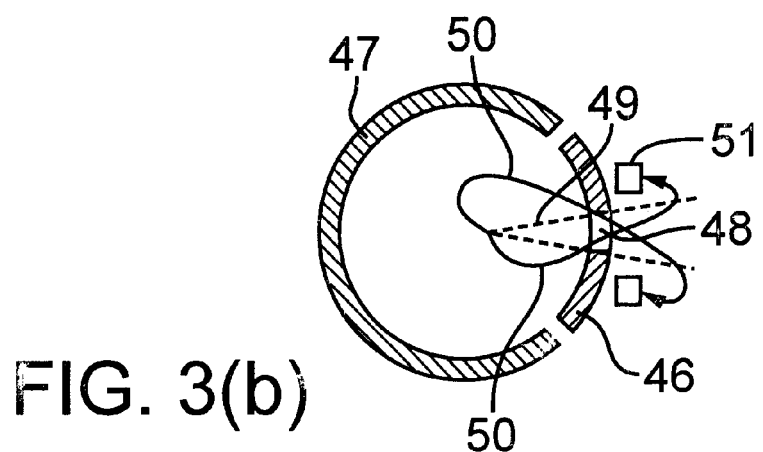

This embodiment is directed to a configuration of SE-detector units and associated deflectors, as shown in FIGS. 3(a)–3(b). In the middle of FIG. 3(a), an entire SE-detector unit 40 is shown in elevational section, flanked on the right and left by respective depicted portions of flanking SE-detector units. Thus, it will be understood that multiple SE-detector units are arrayed in the X- and Y-directions to form an SE-detecting array. The SE-detector array (of which a portion is shown in FIG. 3(a)) can be used as the SE-detector array 12 in the FIG.-1 embodiment. A transverse section along the line A–A' in FIG. 3(a) is shown in FIG. 3(b).

Referring to the SE-detector unit 40 shown in FIG. 3(a), a respective electron beam 41 propagates along a respective axis AX to a respective die 45. The depicted SE-detector unit 40 comprises first and second deflectors 42, 43, respectively, an objective lens 44, an electrode 46 energized with zero volts or a negative voltage, an electrode 47 energized with a positive voltage, a hole 48 defined by the electrode 46, and a detector 51. The electrodes 46, 47 collectively are configured as a cylinder. Hence, each electrode 46, 47 is a respective portion of a cylinder. Secondary electrons 50 emitted from the die 45 propagate along a trajectory 49 to the detector 51.

The SE-detector array of individual SE-detection units has a "detector pitch" in the X-direction equal to the die pitch on the wafer, and a pitch in the Y-direction equal to half the die pitch on the wafer. Each SE-detector unit receives a respective electron beam 41.

In the representative SE-detector unit 40, the electron beam 41 is deflected by the deflectors 42, 43 and passes through the objective lens 44. As deflected, the beam scans individual regions (each approximately 2 mm square) along the X-axis and Y-axis of the die 45.

In each SE-deflector unit 40, the electrodes 46, 47 effectively surround the region on the die 45 irradiated by the beam 41. A positive voltage (typically several tens of volts) is impressed on the electrode 46, and a negative voltage is impressed on the electrode 47.

The region of the die 45 irradiated by the beam 41 produces, as a result of being irradiated, backscattered electrons and secondary electrons. The backscattered electrons have substantially greater kinetic energy than the secondary electrons. As a result, the secondary electrons propagate along straight trajectories 49 that are unaffected by the electrodes 46, 47; hence, the backscattered electrons collide with and are absorbed by the electrodes 46, 47. A small number of backscattered electrons pass through the hole 48 in the electrode 46 (note trajectories 49). However, due to the small size of the hole 48, the number of backscattered electrons passing through it is insignificant.

The secondary electrons are emitted in many directions at relatively low kinetic energy. The secondary electrons tend to be repelled by the electrode 47 and attracted to the electrode 46 (note the trajectory 50). As a result of the high voltage (several KV) imposed on the detector 51 situated outside the electrode 46, secondary electrons attracted by the electrode 46 tend to pass through the hole 48. Passage of secondary electrons through the hole 48 also is facilitated by the strongly convex lens action of the detector 51. Thus, the secondary electrons tend to pass through the hole 48 without being absorbed by the electrode 46, as shown in FIG. 3(*b*) (again, note the trajectories 50). As the secondary electrons are incident on the detector 51, they excite a scintillator inside the detector 51 and cause the scintillator to generate a corresponding amount of light. The light is guided by an optical fiber (not shown) or analogous light guide to an opto-electric converter, such as a photomultiplier (not shown). The opto-electric converter produces a corresponding electrical signal encoding data that are compared with pattern-design data for the die. Thus, the presence or absence of defects in the die is determined.

The detectors 51 are situated in respective positions where backscattered electrons 49 passing through the hole 48 are not incident on the detectors 51. Due to the high kinetic energy of the backscattered electrons, they propagate along straight trajectories and essentially are unaffected by the high voltage impressed on the respective detector 51. Hence, the backscattered electrons are not detected by the detectors 51 and thus do not produce noise. On the other hand, most of the secondary electrons are captured and detected by the respective detector 51. Such a configuration provides excellent signal-to-noise (S/N) ratios, even during operation at high frequencies (500 MHz or more). In addition, there is virtually no crosstalk between individual detectors 51 of the SE-detector array.

As noted above, in this embodiment, the die pitch and beam pitch are equal in the X-direction, as shown in FIG. 3(*a*). Thus, each beam 41 irradiates the same position on the respective die 45. This configuration also allows the data processing necessary for beam control and detection to be identical for each respective SE-detector unit 40.

After imaging has been completed in the area of the die swept by the respective beam, the stage (not shown) on which the wafer is mounted is moved to place new respective regions into position for imaging (within the scanning range of the respective deflectors 42, 43). Thus, so long as the number of dies and the number of detectors in the X-direction are the same, an entire die can be inspected in the X-direction by moving the wafer stage a total distance equal to only one die.

As for the Y-direction, since two beams are irradiated per die in this embodiment, secondary electrons are detected by two detectors, and an inspection corresponding to one die can be accomplished by moving the wafer stage by only one-half of the die pitch on the wafer. If there are twice as many detector units in the Y-direction as there are dies, then all of the dies in the Y-direction can be inspected by moving the wafer stage a total distance of only one-half a die.

By arraying the same number of detectors as the number of dies in the X-direction, and by arraying two times the number of detectors as number of dies in the Y-direction, an entire wafer surface can be inspected in half the time conventionally required to inspect one die. Furthermore, since there is one common set of inspection data in the X-direction and two sets of inspection data in the Y-direction, two sets of reference data are compared with the individual sets of signals from all the detectors. Consequently, if inspection is performed at a speed of 500 MHz, the data-transfer speed can be 2(500 MHz).

As discussed above with respect to the first representative embodiment, the electron beams 41 can be produced simultaneously by a field-emitter array.

Third Representative Embodiment

Figure 4:
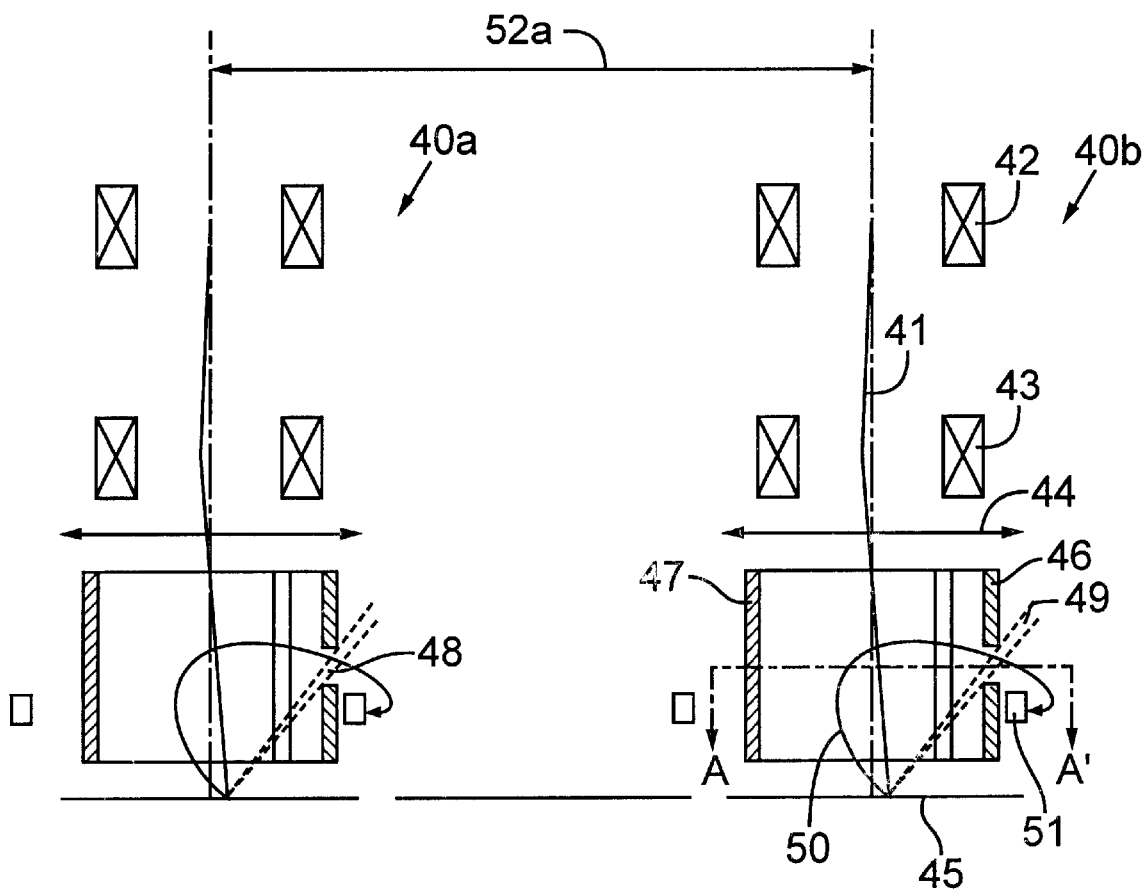
FIG. 4 is an elevational section showing details of two SE-detector units according to the third representative embodiment.

This embodiment is shown in FIG. 4, which depicts two SE-detector units 40*a*, 40*b*. This embodiment differs from the second representative embodiment only in that the beam pitch 52*a* (and thus the pitch of the detector array) is double the die pitch. Hence, components in this embodiment that are the same as corresponding components in the second representative embodiment have the same reference numerals and are not described further.

In view of the configuration of this embodiment, the time required to inspect one wafer is twice the time required by the second representative embodiment. But, since the same locations are being inspected, at any given moment, in each die being inspected, beam control and data processing are common for all dies.

Fourth Representative Embodiment

Figure 5:
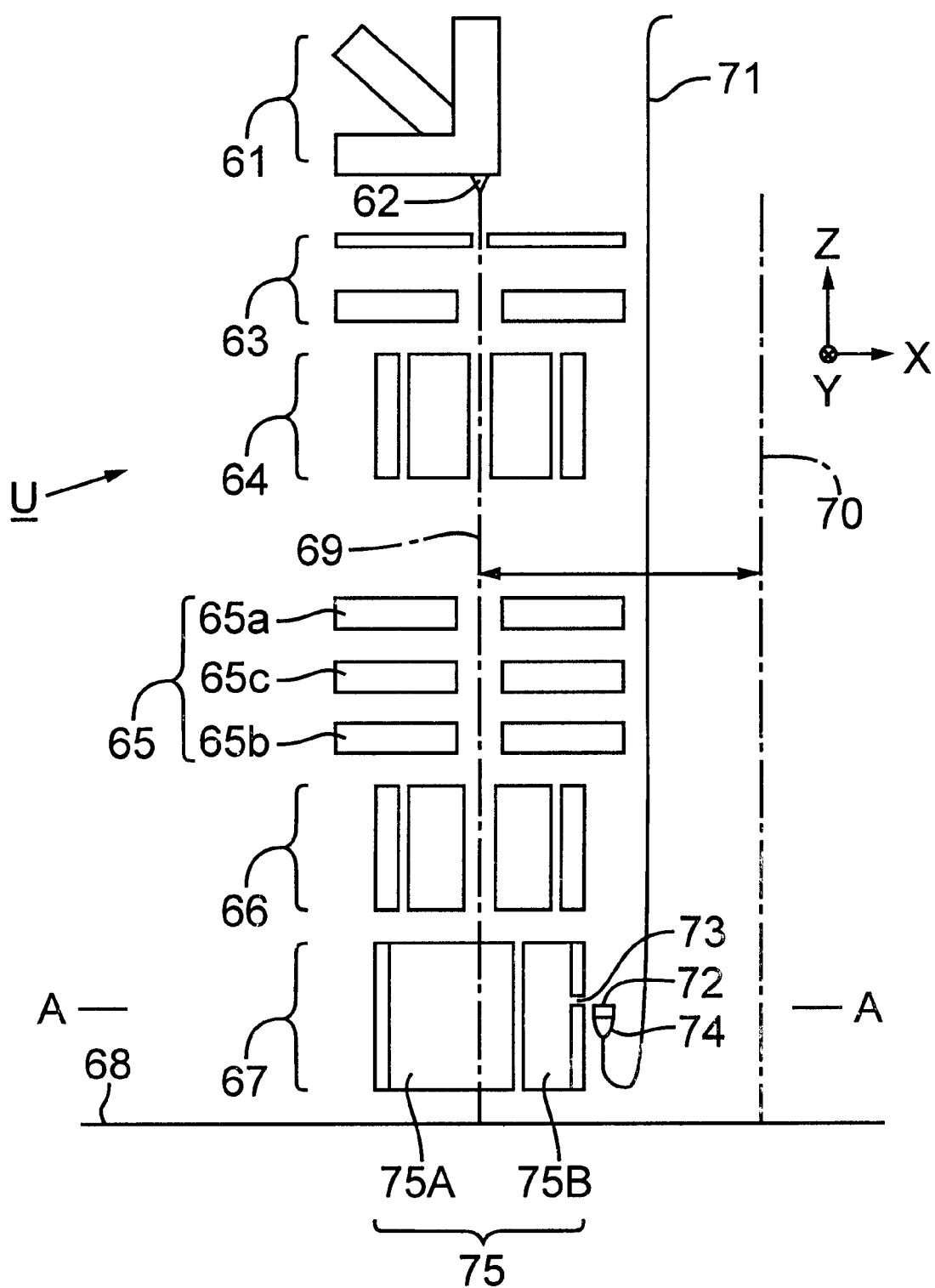
FIG. 5 is a schematic elevational view of certain aspects of an SE-detector column according to the fourth representative embodiment.
Figure 6:
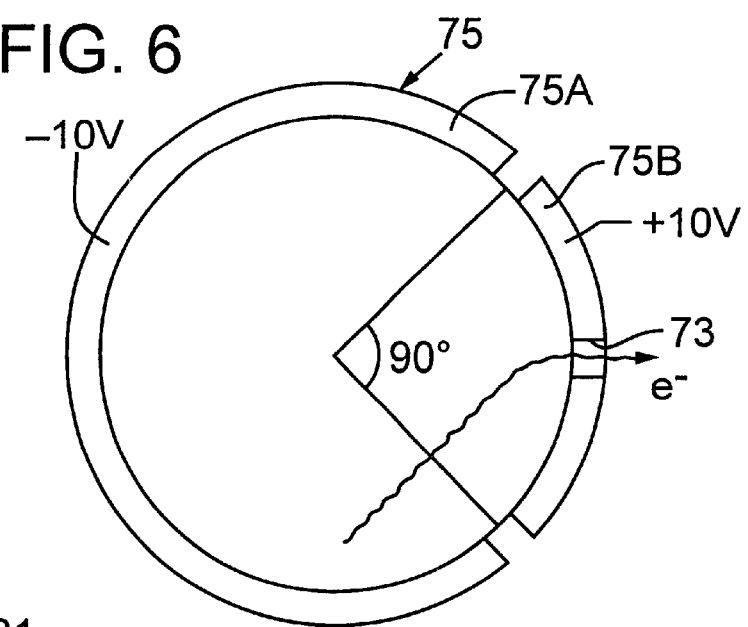
FIG. 6 is a transverse section through the electrode of the SE-detector unit of FIG. 5.
Figure 7:
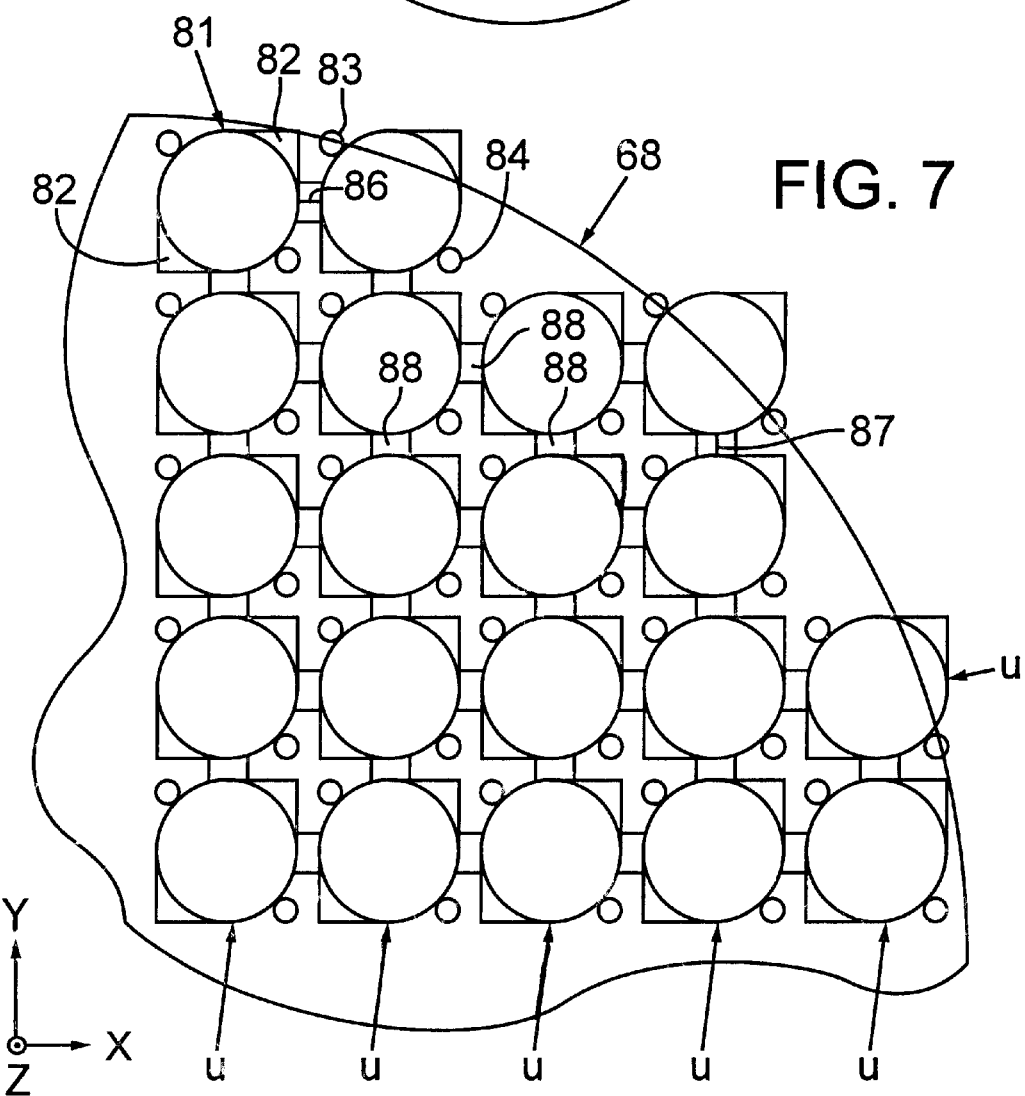
FIG. 7 is a plan view of a portion of the SE-detector array of the fourth representative embodiment.

This embodiment is discussed below in connection with FIGS. 5–7. FIG. 5 is a schematic elevational depiction of an individual channel in a multi-channel electron-beam inspection apparatus; FIG. 6 is a transverse section along the line A—A in FIG. 5 showing the electrodes of the SE-detector unit of a single channel; and FIG. 7 is a plan view of a portion of he array of multiple SE-detector units.

First, the structure of an individual channel U is described, referring to FIG. 5 A micro-drive mechanism 61 comprising piezo-elements (one respective piezo-element for each of X-, Y-, and Z-direction movement) is disposed at the extreme upstream end of the optical axis 69 of the SE-detector unit U. An electron-emission chip 62, which emits an electron beam in a downstream direction, is mounted on the micro-drive mechanism 61. The electron beam emitted from the electron-emission chip 62 is focused by downstream optics (including a condenser lens 63) as a spot within a respective die on a wafer 68.

The micro-drive mechanism 61 is operable to move the electron-emission chip 62 minutely in the X-, Y-, and Z-directions. Motions in the X- and Y-directions allow alignment of the electron beam with the potential center of the condenser lens 63. The crossover magnification of the electron beam can be adjusted by causing the micro-drive mechanism 61 to move the electron-emission chip 62 in the Z-direction.

An electrostatic deflector 64 comprising at least four poles is situated downstream of the condenser lens 63. An objective lens 65 is situated downstream of the deflector 64. The objective lens 65 desirably is an electrostatic lens having three electrodes 65*a*, 65*b*, 65*c*. The upper and lower electrodes 65*a*, 65*b*, respectively, are ground-potential electrodes that have zero potential (0 V) during use. The center electrode 65*c* can be charged with a positive or negative voltage as required. An electrostatic octapole deflector 66 is disposed downstream of the objective lens 65. The electron beam is deflected by the octapole deflector 66 as required to scan the beam (focused to a spot) on the respective die on the wafer 68. As the wafer surface is irradiated, secondary electrons are produced that propagate away from the irradiated surface.

Since the condenser lens 63, objective lens 65, and deflectors 64, 66 in this embodiment are electrostatic, the size of each channel U can be kept adequately small.

A respective SE-detector unit 67 is situated downstream of the octapole deflector 66. The SE detector 67 comprises an electrode 75, a scintillator 72, and a light guide 71. The electrode 75 gathers secondary electrons and keeps them from escaping to an adjacent channel (denoted by the axis 70). The cylindrical electrode 75 is divided into two portions 75A, 75B. The larger portion 75A extends around ¾ of the circumference of the electrode 75, and the smaller portion 75B extends around the remaining ¼ of the circumference. Hence, the relative size of the portion 75A to the portion 75B is a ratio of 3:1 in this embodiment. A negative voltage (e.g., −10 V) is impressed on the larger electrode portion 75A, and a positive voltage (e.g., +10 V) is impressed on the smaller electrode portion 75B. The smaller electrode portion 75B defines a small (e.g., 1-mm diameter) through-hole 73.

The scintillator 72 is located outside the smaller electrode portion 75B at a location that is away from a straight-line trajectory through the hole 73 from the point of incidence of the electron beam on the wafer 68. The scintillator 72 converts incident secondary electrons to respective units of light. The surface of the scintillator 72 includes a thin layer of aluminum charged during use with a voltage of 10 KV. The scintillator 72 also includes a "sub-stage" condenser 74 to which is attached an end of the light guide 71. The light guide 71 transmits light from the scintillator 72 for remote conversion into a corresponding electrical signal.

On the wafer 68, multiple dies are formed at a predetermined pitch. The wafer can be any of various convenient diameters, including 12-inch diameter.

Referring now to FIG. 7, a quadrant of multiple individual channels U is shown. The various components of an individual channel U shown in FIG. 5 are contained inside each respective column 81 having a transverse profile of no greater than 30-mm square. Thus, each channel U can correspond with a respective individual die on the wafer 8. Each column 81 is supported by a pair of supports 82 flanking the column 81. The supports 82 extend upward (in the Z-direction) beyond the distal end of the respective column 81. The supports 82 are secured relative to each other by positioning members (not shown). The end of a respective column 82 can be set to a particular desired position in the Z-direction by removing clamps (not shown).

In this embodiment, two individual cables 83, 84 are associated with each column 81. The cable 83 is a combination of a signal cable for the deflectors 64, 66 and the sub-stage condenser 74 of the light guide 71. The cable 84 is a combination of cables from respective power supplies (not shown) connected to the lenses 63, 65, and from an axial-alignment power supply (not shown) to the piezo-elements of the respective micro-drive mechanism 61.

Multiple columns 81, as described above, are disposed in an ordered array, at a predetermined pitch, in the X- and Y-directions, as shown in FIG. 7. Actuators 88 are mounted between adjacent columns 81. After removing the clamps, the spacing in the X-direction (denoted by line 86) and the spacing in the Y-direction (denoted by the line 87) for each column 81 can be adjusted by moving the actuators 88 until the dimensions reach zero.

An individual channel U operates as follows. Referring to FIG. 5, a respective electron beam is emitted in a downstream direction from the electron-emission chip 62. The electron beam is focused by the condenser lens 63 and deflected as required by the electrostatic deflector 64 so that the beam aligns with the optical axis 69 of the channel U. If required, the micro-drive mechanism 61 is actuated to move the electron-emission chip 62 in the X- and Y-directions to align the electron beam with the potential center of the electromagnetic lens 63. The micro-drive mechanism 61 is moved as required in the Z-direction to adjust the crossover magnification of the electron beam.

The electron beam exiting the electrostatic deflector 64 is again focused by the objective lens 65 to focus the beam to a spot on the wafer 68. The electrostatic deflector 66 is actuated as required to scan the beam spot over the respective die region on the wafer 68. Secondary electrons are emitted from the irradiated region on the wafer.

The larger electrode portion 75A is energized with −10 V (FIG. 6), which causes secondary electrons emitted from the wafer 68 to be repulsed by the larger electrode portion 75A. The repulsed secondary electrons pass through the hole 73 in the smaller electrode portion 75B. Meanwhile, backscattered electrons emitted from the wafer 68 are absorbed by the electrode 75 and do not exit through the hole 73. In this manner, backscattered electrons are distinguished from secondary electrons, thereby improving the resolution with which secondary electrons are detected.

The secondary electrons exiting through the hole 73 are converted to light by the scintillator 72. The light is condensed by the sub-stage condenser 74 and conducted to a detector (not shown) by the light conductor 71, which converts the light to a corresponding electrical data signal. Thus, the secondary electrons from each die are collected and converted to corresponding data by the respective SE-detector units without escaping outside the respective SE-detector unit 67. At the same time, incursion of secondary electrons from adjacent channels is prevented.

As noted above, the dies on the wafer 68 are arranged by rows and columns. When beginning inspection of a wafer 68, the row pitch and column pitch of the individual channels U of the SE-detector array are adjusted as required by the actuators 88 to 1/n (wherein n is an integer) the row pitch and column pitch, respectively, of the wafer 68. Then, the individual beams of the channels U are made incident on the wafer 68 at the same position in each respective die. With respect to any two dies, the presence or absence of a defect in one of the dies is indicated if a difference or no difference, respectively, is detected in the signals produced by the respective SE-detector units. In other words, if a difference is detected in the signals from two channels, then a defect is indicated in one or the other of the respective dies. If no difference is detected in the signals, then no defect is evident. Inspection of the wafer 68 can be performed by making the pitch of the individual channels U the same as, or an integer multiple of, the die pitch on the wafer 68, and by making the beam of each of the various channels incident to the same position in each of the dies in at least two different locations on the wafer. Because of this, inspection is possible even when the data transfer is less than the number of channels. Specifically, data transfer is unnecessary when comparing the presence or absence of a difference in the signals from two locations.

Respective beams can be caused to be incident to the same location in respective dies at three or more different locations on the wafer 68. In such an instance, the presence of defects in the dies can be determined by comparing the signals produced by secondary electrons emitted from the points of incidence in these dies at three or more locations. The die containing the defect is determined by comparing the signals from the three or more locations.

Fifth Representative Embodiment

Figure 8:
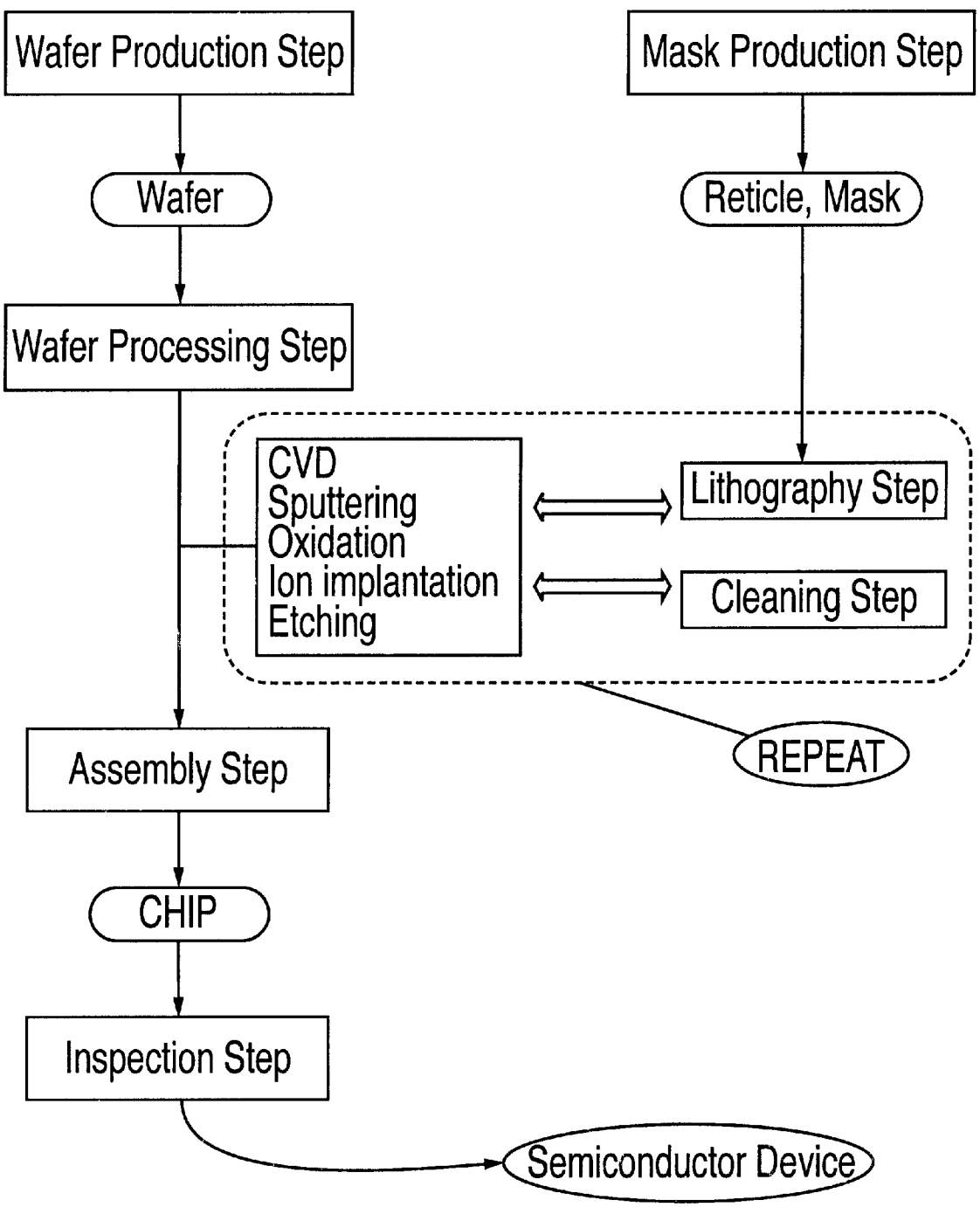
FIG. 8 is a block diagram of a semiconductor-processing method according to the fifth representative embodiment.

This embodiment is directed to a semiconductor-device manufacturing method. The method, as diagrammed in FIG. 8, generally comprises the main steps of wafer production (wafer preparation), reticle production (reticle preparation), wafer processing, device (chip) dicing and assembly, and inspection of completed chips. Each step usually comprises several sub-steps.

Among the main steps, wafer processing is key to achieving the smallest feature sizes (critical dimensions), best inter-layer registration, and device performance. In the wafer-processing step, multiple circuit patterns are layered successively atop one another in each die on the wafer, wherein the formation of each layer typically involves multiple sub-steps. Usually, many operative semiconductor devices (chips or dies) are produced on each wafer.

Typical wafer-processing steps include: (1) Thin-film formation involving formation of a dielectric layer for electrical insulation or a metal layer for connecting wires. The films are produced by CVD, sputtering, or other suitable technique. (2) Oxidation of a thin-film layer. (3) Microlithography to form a resist pattern, according to the reticle pattern, for selective processing of the thin film or the substrate itself. (4) Etching or analogous step to etch the thin film or substrate according to the resist pattern. (5) Doping as required to implant ions or impurities into the thin film or substrate according to the resist pattern. (6) Resist stripping to remove the resist from the wafer. (7) Wafer inspection. Wafer processing is repeated as required (typically many times) to fabricate the desired semiconductor chips on the wafer.

Figure 9:
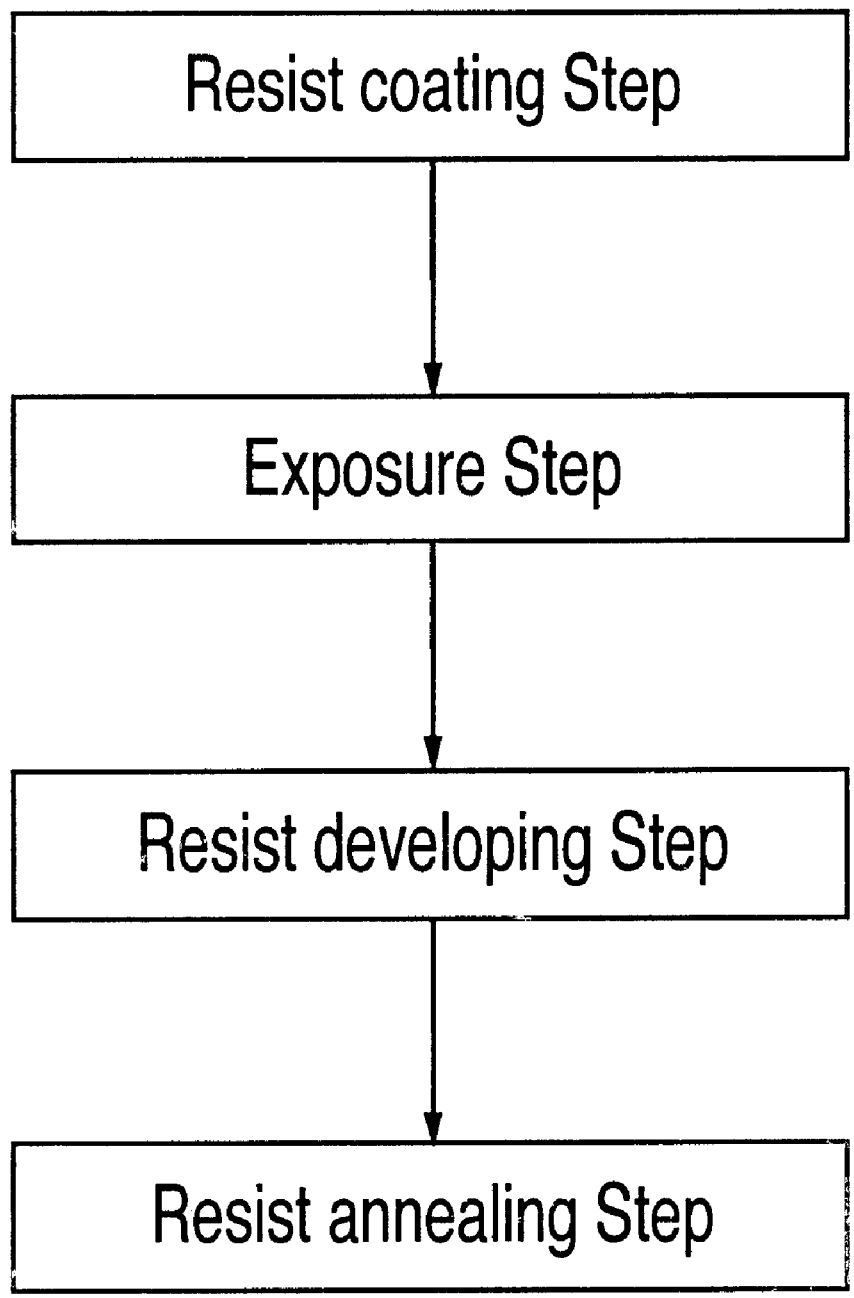
FIG. 9 is a block diagram of steps of the microlithography step of the FIG.-8 method.

FIG. 9 is a flow chart of typical steps performed in microlithography, which is a principal step in wafer processing. The microlithography step typically includes: (1) application of resist to the wafer, wherein a suitable resist is coated on the wafer substrate (which can include a circuit element formed in a previous wafer-processing step); (2) exposure step, to expose the resist with the desired pattern and form a latent image; (3) development step, to develop the exposed resist; and (4) optional annealing step, to stabilize the developed pattern in the resist.

Defect-inspection methods and apparatus according to the invention can be used in the inspection step summarized above. Even semiconductor devices having extremely fine patterns can be inspected with good throughput, even when all dies are inspected. This facilitates improving the yield of finished product and avoiding shipments of defective product.

Sixth Representative Embodiment

This embodiment is directed to a method for manufacturing semiconductor devices, wherein the method includes a wafer-inspection apparatus as described above.

Figure 10:
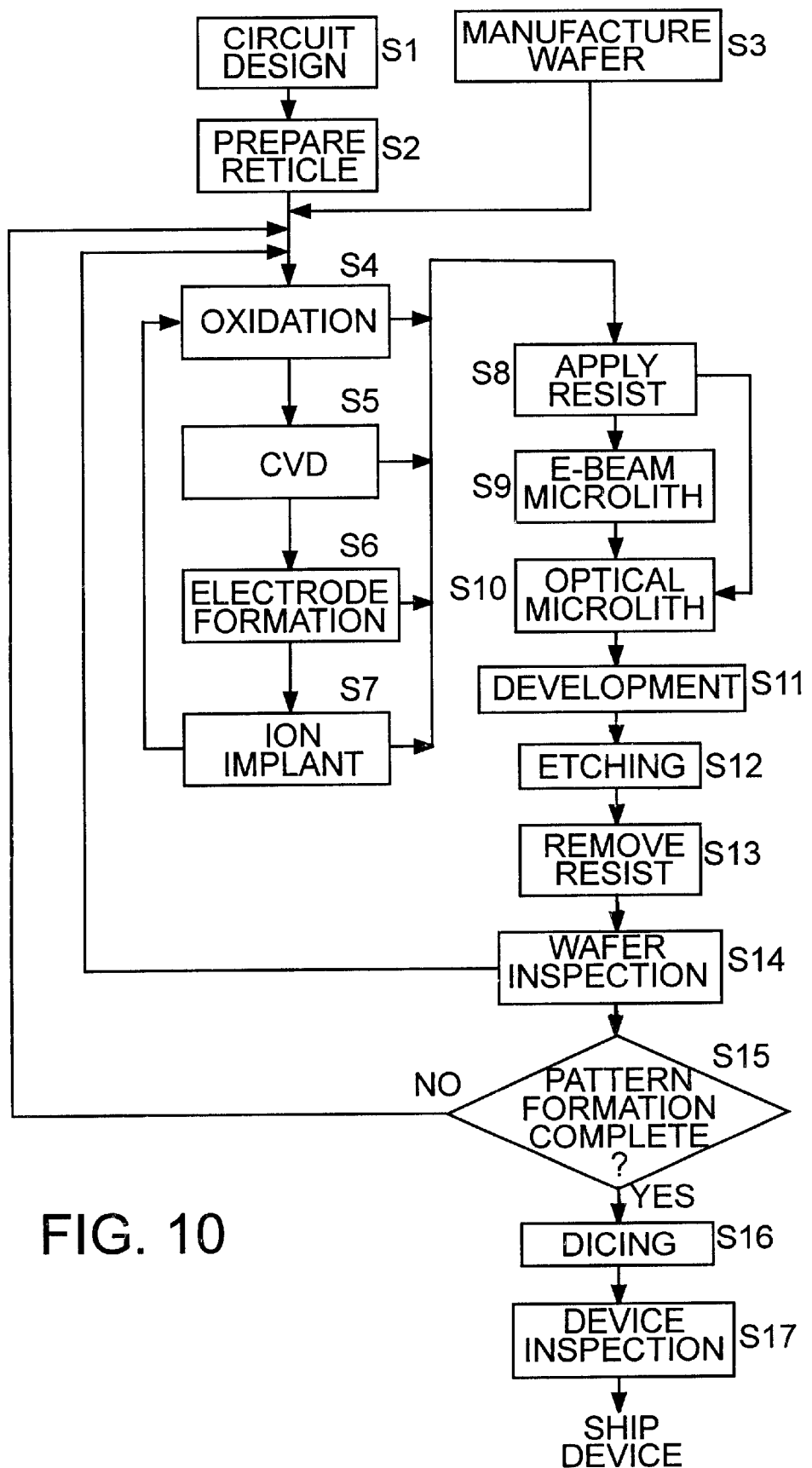
FIG. 10 is a block diagram of a semiconductor-processing method according to the sixth representative embodiment.

A flow chart of the method is shown in FIG. 10. This method is especially suitable for manufacturing semiconductor integrated circuits of the LSI, VLSI, and ULSI categories; ICD panels, CCDs, thin-film electromagnetic heads, micro-machines, etc.

In step S1, a circuit design is prepared for the semiconductor device. In step S2, a reticle defining the circuit pattern is designed an prepared. The pattern can include, for certain elements of the pattern, local resizing to achieve correction of proximity effects when the pattern is projected microlithographically onto a wafer. In step S3, a wafer is manufactured using a material such as silicon. In step S4, the surface of the wafer is oxidized. In step S5, an insulating film is formed on the surface of the wafer. In step S6, electrodes are formed on the wafer by localized metal deposition. In step S7, the wafer is bombarded with ions to dope certain regions of the surface. The sequence of steps from step S4 through step S7 is repeated in whole or in part, in the stated order or in an altered order, as required.

In step S8, a photosensitive agent ("resist") is applied to the wafer surface. In step S9, the circuit elements defined by the reticle are microlithographically exposed onto the resist using an electron-beam microlithography apparatus and the reticle prepared in step S2. Exposures to correct proximity effects may be performed before or after step S9, which can help make emission of backscattered electrons from the wafer more uniform. In step S10, the circuit elements defined by the reticle are exposed microlithographically onto the resist using an optical microlithography apparatus (e.g., optical stepper) and the reticle prepared in step S2. One or the other of steps S9 and S10 may be omitted as required.

In step S11, the exposed wafer is developed. In step S12, portions of the wafer other than regions coated with the image in the resist are etched away selectively. In step S13, etching is completed nd remaining resist is removed. In step S14, the wafer is inspected using an inspection apparatus as described above to determine whether etching was completed successfully. Any defective chips on the wafer are detected.

Multiple-layered circuit patterns are formed on the wafer by repeating steps S4 through S13, and step S14, as required. In step S15, it is determined whether pattern formation is completed. If pattern formation is complete, the wafer processing proceeds to step S16 to begin the final phase of processing. In step S16, the wafer is diced into individual chips. This step also includes device assembly (including lead bonding, etc.) and device packaging. In step S17, the finished semiconductor devices are inspected by operational and durability tests. Devices that pass the tests are shipped.

As is clear from the discussion above, the present invention provides multi-channel electron-beam inspection apparatus and methods that achieve substantial improvements in semiconductor-device inspections at substantially higher throughput.

Whereas the invention has been described in connection with multiple representative embodiments, it will be understood that the invention is not limited to those embodiments. On the contrary, the invention is intended to encompass all modifications, alternatives, and equivalents as may be included within the spirit and scope of the invention, as defined by the appended claims.

What is claimed is:

1. An apparatus for inspecting a surface of a specimen, the apparatus comprising:
    an emitter array comprising multiple charged-particle emitters each configured to emit simultaneously a separate individual charged particle beam along a separate respective beam axis;
    first and second electromagnetic lenses situated downstream of the emitter array and configured to focus simultaneously the individual charged particle beams, from the emitter array, onto respective loci on the surface of the specimen so as to cause each of the loci to emit secondary electrons;
    a secondary-electron (SE)-detector array comprising multiple SE-detector units each situated and configured to receive and detect secondary electrons from a respective locus on the specimen; and
    a deflector situated between the first and second electromagnetic lenses and configured to deflect the charged particle beams and cause the beams to scan simultaneously respective regions on the surface corresponding to the respective loci.

2. The apparatus of claim 1, wherein the first and second electromagnetic lenses are configured as a symmetric magnetic doublet.

3. The apparatus of claim 2, wherein the symmetric magnetic doublet is a magnifying lens or 1:1 lens.

4. The apparatus of claim 2, wherein the symmetric magnetic doublet further comprises a magnification-adjusting lens.

5. The apparatus of claim 1, wherein the charged-particle emitters are in an X-Y plane, and the beam axes extend in a Z-direction.

6. The apparatus of claim 1, wherein:

the beam axes extend in a Z-direction; and the charged-particle emitters of the emitter array are displaced individually from an X-Y plane, perpendicular to the Z-direction, so as to correct curvature of an image collectively formed on the specimen by the charged particle beams passing through the first and second electromagnetic lenses.

7. The apparatus of claim 1, wherein:

the specimen extends in an X-direction and a Y-direction;

the loci are arrayed on the surface of the specimen with an X-direction pitch and a Y-direction pitch; and at least one of the X-direction pitch and the Y-direction pitch is adjustable.

8. The apparatus of claim 1, wherein:

each SE-detector unit in the SE-detector array comprises a respective detector electrode in surrounding relationship to the respective beam axis, the detector electrodes each being energized with a respective voltage;

each detector electrode defines a respective through-hole;

each SE-detector unit comprises an SE detector situated outside the respective detector electrode adjacent the through-hole; and each SE detector is charged with a voltage that is more positive than the respective voltage with which the respective detector electrode is energized, so as to draw secondary electrons through the through-hole to the respective SE detector.

9. The apparatus of claim 8, wherein:

each through-hole has an angular orientation about the respective beam axis; and the angular orientations of the through-holes are identical for all SE detectors of the SE-detector array.

10. The apparatus of claim 1, wherein:

each SE-detector unit comprises a respective SE detector and scintillator associated with the SE detector; and each scintillator is connected by a light guide to a photodetector.

11. The apparatus of claim 10, further comprising a vacuum chamber surrounding the emitter array, the first and second electromagnetic lenses, the SE-detector array, and the deflector, the vacuum chamber comprising a window, wherein light from the light guide is transmitted to the photodetector through the window.

12. The apparatus of claim 1, wherein each SE-detector unit further comprises a respective scanning-position deflector configured to scan the respective charged particle beam within a respective area, corresponding to the respective locus, on the surface of the specimen.

13. The apparatus of claim 12, wherein the respective scanning-position deflector is situated upstream or downstream of the respective SE detector.

14. The apparatus of claim 1, wherein the emitter array comprises multiple electron-beam emitters.

15. A method for inspecting a surface of a specimen, comprising:

producing multiple separate individual charged particle beams each propagating along a respective beam axis;

simultaneously focusing the individual charged particle beams onto respective loci on the specimen surface so as to cause each of the loci to emit secondary electrons;

while focusing the beams, simultaneously deflecting the charged particle beams so as to cause each beam to scan a respective region corresponding to the respective locus;

detecting the secondary electrons produced from each region so as to produce respective signals pertaining to the secondary electrons emitted from the regions; and analyzing the signals to produce data from which an image of the scanned regions of the surface can be formed.

16. In a process for manufacturing semiconductor devices on a wafer substrate, a method for inspecting the wafer substrate, comprising the inspection method of claim 15.

17. A semiconductor device produced by the process of claim 16.

18. An apparatus for inspecting a surface of a specimen, the apparatus comprising:

means for simultaneously emitting multiple charged particle beams along respective beam axes;

projection-lens means for simultaneously focusing the charged particle beams onto respective loci on the surface of the specimen to cause each locus to emit secondary electrons;

secondary-electron (SE)-detection means for receiving and detecting the secondary electrons; and deflector means for deflecting the charged particle beams and causing the beams to scan simultaneously respective regions on the surface corresponding to the respective loci.

19. An apparatus for inspecting a surface of a substrate, extending in an X-direction and a Y-direction, on which multiple dies have been formed at an X-direction die pitch and a Y-direction die pitch, the apparatus comprising:

an emitter array comprising multiple charged-particle emitters each configured to emit a separate individual charged particle beam along a respective beam axis extending in a Z-direction, the beams having an X-direction beam pitch and a Y-direction beam pitch;

a projection-lens system situated and configured to focus simultaneously the individual charged particle beams, from the emitter array, onto respective loci on the surface of the substrate so as to cause the loci to emit secondary electrons; and a secondary-electron (SE)-detector array comprising multiple SE-detector units each situated and configured to receive and detect secondary electrons from a respective locus on the substrate, wherein at least one of the X-direction die pitch and Y-direction die pitch is an integer multiple or integer fraction of the X-direction beam pitch and Y-direction beam pitch, respectively.

20. An apparatus for inspecting a surface of a substrate, extending in an X-direction and a Y-direction, on which multiple dies have been formed uniformly spaced at a die pitch, the apparatus comprising:

an emitter array comprising multiple charged-particle emitters each configured to emit a separate individual charged particle beam along a respective beam axis extending in a Z-direction, the beams being spaced from each other at a beam pitch;

multiple secondary-electron (SE) columns situated and configured to direct a respective individual charged particle beam to a respective locus on the surface of the substrate so as to cause the loci to emit secondary electrons; and each SE column comprising a respective SE-detector unit situated and configured to receive and detect secondary electrons from the respective locus.

21. An apparatus for inspecting a surface of a substrate on which multiple dies have been formed spaced apart from one another at a uniform die pitch, the apparatus comprising:

a field-emitter array comprising multiple electron emitters each configured to emit a separate individual electron beam along a respective beam axis;

a projection-lens system situated and configured to focus simultaneously the individual electron beams, from the field-emitter array, onto respective loci on the surface of the substrate so as to cause the loci to emit secondary electrons; and a secondary-electron (SE)-detector array comprising multiple SE-detector units each situated and configured to receive and detect secondary electrons from a respective locus on the substrate.

22. An apparatus for inspecting a surface of a substrate, comprising:

multiple charged-particle-beam channels situated and configured to emit simultaneously multiple charged particle beams each along a respective beam axis to a respective locus on the substrate surface so as to cause the loci to emit secondary electrons, the channels being arranged at a channel pitch in an X-direction and a Y-direction, the X- and Y-directions being perpendicular to a Z-direction to which the beam axes are parallel;

each channel comprising a charged-particle-beam (CPB) source, CPB lenses situated and configured to focus the respective beam as a respective beam spot on the respective locus, a deflector situated and configured to scan the beam spot within a respective region associated with the locus on the substrate surface, and a secondary-electron (SE) detector situated and configured to detect the secondary electrons emitted from the respective region; and a pitch-adjustment mechanism associated with the channels and configured so as to change the channel pitch in at least one of the X- and Y-directions.

23. The apparatus of claim 22, wherein:

the substrate is a semiconductor wafer on which multiple dies have been formed at a die pitch; and the pitch-adjustment mechanism is configured to adjust the channel pitch to 1/n of the die pitch, wherein n is an integer.

24. The apparatus of claim 22, wherein each channel has an outside dimension of no greater than 30 mm in the X-direction or Y-direction.

25. The apparatus of claim 22, wherein at least one of the CPB lenses and deflectors is electrostatic.

26. The apparatus of claim 22, wherein at least one of the CPB lenses and deflectors is electromagnetic.

27. The apparatus of claim 22, wherein each SE detector comprises:

an electrode defining a through-hole, the electrode being energized to be positively charged; and a scintillator situated adjacent the through-hole but downstream with respect to the secondary electrons emitted from the respective region, the scintillator further being situated such that backscattered electrons from the respective region and propagating along a linear trajectory through the through-hole do not impinge on the scintillator.

28. The apparatus of claim 27, further comprising a condenser element situated and configured to collect and focus light produced by the scintillator.

29. The apparatus of claim 28, further comprising an optical fiber connected to the condenser element.

30. A method for inspecting a surface of a specimen on which multiple dies have been formed at a die pitch extending in an X-direction and a Y-direction, the method comprising:

producing multiple separate individual charged particle beams each propagating along a respective beam axis perpendicular to the X- and Y-directions, the beam axes being arranged at a channel pitch;

simultaneously focusing the individual beams onto respective loci on the specimen surface so as to cause the loci to emit secondary electrons;

while focusing the beams, simultaneously scanning the charged particle beams over respective regions corresponding to the respective locus;

collecting and detecting the secondary electrons produced from each region; and adjusting the channel pitch to be 1/n of the die pitch, wherein n is an integer.

31. The method of claim 30, further comprising the steps of:

producing respective signals pertaining to the secondary electrons emitted from the regions; and analyzing the signals to produce data from which an image of the scanned regions of the surface can be formed.

32. The method of claim 31, further comprising the steps of:

causing at least two beams to be incident at a same position in separate respective dies on the specimen; and comparing the signals produced by secondary electrons emitted from the separate respective dies to determine any difference between the signals indicating a difference in the respective dies.

33. The method of claim 31, further comprising the steps of:

causing at least three beams to be incident at a same position in separate respective dies on the specimen; and comparing the signals produced by secondary electrons emitted from the separate respective dies to determine any difference in the signals indicating a difference in the respective dies.

34. In a process for manufacturing semiconductor devices on a wafer substrate, a method for inspecting the wafer substrate, comprising the inspection method of claim 30.

35. A semiconductor device produced by the method of claim 34.

* * * * *

UNITED STATES PATENT AND TRADEMARK OFFICE
CERTIFICATE OF CORRECTION

PATENT NO. : 6,465,783 B1
DATED : October 15, 2002
INVENTOR(S) : Nakasuji

It is certified that error appears in the above-identified patent and that said Letters Patent is hereby corrected as shown below:

Column 9,
Line 4, "1 1" should be -- 11 --.
Line 58, "now" should be -- no --.

Column 12,
Line 3, "1 1" should be -- 11 --.

Column 14,
Line 25, "FIG. 5" should be -- FIG. 5. --.

Column 17,
Line 48, "an" should be -- and --.

Column 18,
Line 8, "nd" should be -- and --.

Signed and Sealed this

Fourth Day of November, 2003

JAMES E. ROGAN
*Director of the United States Patent and Trademark Office*